United States Patent [19]

Krimm et al.

[11] 4,307,032
[45] Dec. 22, 1981

[54] PROCESS FOR THE PREPARATION OF DIALKYL CARBONATES

[75] Inventors: Heinrich Krimm; Hans-Josef Buysch; Hans Rudolph, all of Krefeld, Fed. Rep. of Germany

[73] Assignee: Bayer Aktiengesellschaft, Leverkusen, Fed. Rep. of Germany

[21] Appl. No.: 149,388

[22] Filed: May 13, 1980

Related U.S. Application Data

[63] Continuation of Ser. No. 938,185, Aug. 30, 1978, abandoned.

[30] Foreign Application Priority Data

Sep. 7, 1977 [DE] Fed. Rep. of Germany ....... 2740251

[51] Int. Cl.$^3$ .............................................. C07C 68/06
[52] U.S. Cl. .................................................. 260/463
[58] Field of Search ........................................ 260/463

[56] References Cited

U.S. PATENT DOCUMENTS 3,248,414  4/1966  Stevens ............................... 260/463
3,506,619  4/1970  Stewart et al. ...................... 528/277
3,642,858  2/1972  Frevel et al. ......................... 260/463
3,689,462  9/1972  Maximovich ....................... 260/463
3,803,201  4/1974  Gilpin et al. ........................ 260/463

FOREIGN PATENT DOCUMENTS 2107084  9/1972  Fed. Rep. of Germany .
2637409  3/1977  Fed. Rep. of Germany .

OTHER PUBLICATIONS

H. Zondler et al., Chem. Abstracts 85: 108507q (1976).
K. Chimura et al., Chem. Abstracts 78:97345n (1973).
H. Zondler et al., Helv. Chim. Acta, vol. 60, 6 (1977), Nr. 181, pp. 1845 et seq.

Primary Examiner—Donald G. Daus
Assistant Examiner—M. C. Eakin
Attorney, Agent, or Firm—Sprung, Felfe, Horn, Lynch & Kramer

[57] ABSTRACT

A process for preparing a dialkyl carbonate by contacting a glycol carbonate with an alcohol at an elevated temperature in the presence of a thallium compound.

7 Claims, No Drawings

PROCESS FOR THE PREPARATION OF DIALKYL CARBONATES

This is a continuation of application Ser. No. 938,185 filed Aug. 30, 1978, now abandoned.

The present invention relates to a process for the preparation of dialkyl carbonates by reacting glycol carbonates with alcohols in the presence of thallium compounds.

The preparation of dialkyl carbonates by transesterifying alkylene carbonates with alcohols in the presence of alkali metals or alkali metal compounds is known from U.S. Pat. No. 3,642,858. The preferred use of sodium alcoholates as the catalyst suggests their particular suitability. Temperatures between 175° and 225° C. are given as typical reaction temperatures. According to Example 3 in the table in the U.S. Patent Specification, lower temperatures lead to only low conversions, even with relatively long reaction times. However, if the preferred high reaction temperatures are used, side-reactions which lower the yield and make working up difficult take place, in some cases to a considerable extent. Such side-reactions take place, in particular, in the case of aliphatic carbonates, which are less stable. Above all, these readily split off carbon dioxide, ethers being formed. Such side-reactions preferably take place between dialkyl carbonates and 1,2-glycols, and particularly readily between glycol carbonates and 1,2-glycols, when the proportion of glycol increases in the course of the trans-esterification. The by-products which are formed are, above all, alkyl glycol ethers and polyglycols, such as di-, tri- and tetra-glycols.

Furthermore, a process for the preparation of dialkyl carbonates by trans-esterifying cyclic carbonates with alcohols in the presence of tertiary amines at temperatures between 50° and 150° C. is described in DT-OS (German Published Specification) No. 2,615,665. The disadvantage of this process is the large amount of tertiary amines which are required as the catalyst. Since the tertiary amines themselves are volatile, they are difficult to separate off from the reaction components. In spite of the large amounts of catalyst, the trans-esterification according to the process of DT-OS (German Published Specification) No. 2,615,665 proceeds relatively slowly. Accordingly, in order to accelerate the reaction, the temperature would have to be raised. However, private experiments have shown that the rate of reaction then indeed increases, but at the same time side-reactions in the sense described above increasingly take place.

SUMMARY OF INVENTION

It has now been found, surprisingly, that the reaction of glycol carbonates with alcohols to give dialkyl carbonates can be carried out under far milder conditions and in a very much shorter time than is known from the state of the art if thallium compounds are used as the catalysts. With respect to this reaction, thallium compounds have an exceptionally favorable temperature coefficient, which causes a very rapid rise in rate with only a slight increase in temperature.

This is surprising inasmuch as thallium compounds are indeed known as trans-esterification catalysts, but have not been described in connection with carbonates.

Furthermore, it is also surprising that, in contrast to other trans-esterification catalysts, thallium compounds suppress the side-reactions under otherwise identical conditions.

The present invention relates to a process for the preparation of dialkyl carbonates by reacting glycol carbonates with alcohols at elevated temperature in the presence of catalysts, which is characterised in that the reaction is carried out in the presence of a thallium compound as the catalyst.

Compared with the state of the art, the process according to the invention has the following advantages:

The amounts of catalyst can be low. They need only be a fraction of the amount customarily used, which means that the catalyst can be separated off from the reaction mixture without difficulty and can be re-used. The decompositions, caused by high concentrations of the catalyst, during the working up of the products by distillation are avoided. The reaction temperatures can be kept comparatively low, which contributes to the increase in the efficiency of the process. The rate of reaction is exceptionally high and enables the trans-esterification equilibrium to be set up in a very short time, which ensures a high space/time yield. Side-reactions, such as the formation of polyglycols, are virtually completely suppressed and yield losses are thus avoided.

Starting materials which are employed in the process as alcohols according to the invention are, on the one hand, aliphatic and/or cycloaliphatic hydroxy compounds especially alkanols and cycloalkanols with 1 to 10 carbon atoms, such as methanol, ethanol, propanol, isopropanol, n-butanol, isobutanol, allyl alcohol, cyclohexanol, ethylhexanol, benzyl alcohol and methylglycol. Thus, the alcohols can be mono-ols or polyols e.g. diols. The carbonate reactants indude carbonates of 1,2-diols with 2 to 4 carbon atoms, such as butylene glycol carbonate, vinyl-ethylene glycol carbonate, chloromethyl-ethylene glycol carbonate, and particularly preferably ethylene glycol carbonate and propylene glycol carbonate.

Aliphatic and/or cycloaliphatic hydroxy compounds with 1 to 6 C atoms are preferably employed, those with 1 to 4 C atoms being particularly preferred.

The molar ratio of the reactants is not very decisive. The alcohol can be used either in an amount which is less than the molar (stoichiometric) amount or in excess. However, an excess of alcohol of about 1 to 10 mols per mol of glycol carbonate is advisable in order to shift the equilibrium in the direction of the desired carbonate. One can, of course employ a larger excess. Suitable catalysts include thallium compounds such as thallium-I oxide, thallium-III oxide, thallium-I hydroxide, thallium-I carbonate, thallium-I acetate, thallium-III acetate, thallium-I bromide, thallium-I chloride, thallium-III chloride, thallium-I fluoride, thallium-I formate, thallium-I nitrate, thallium-I cyanate, thallium-I stearate, thallium-I naphthenate, thallium benzoate, thallium cyclohexylphosphonate, thallium-I hexahydrobenzoate, cyclopentadienylthallium, thallium methylate and thallium ethylate.

The following thallium compounds are preferably employed: thallium-I oxide, thallium-I hydroxide, thallium-I carbonate, thallium-I acetate, thallium-III acetate, thallium-I fluoride, thallium-I formate, thallium-I nitrate, thallium-I naphthenate and thallium methylate.

The amounts of catalyst are not critical. In general, they are about 10 to 0.0001% by weight, preferably 0.001 to 1% by weight, relative to the reaction mixture.

The reaction temperatures are in the range from about 50° to 250° C., and are preferably 60° to 220° C. and particularly preferably 120° to 200° C.

The residence time necessary in the reactor depends on the temperature. It is between a good 10 hours at a low temperature and a few seconds at higher temperatures, preferably in the range from 0.1 to 20 minutes. It can, however, be extended without danger of by-products being formed.

The process according to the invention is preferably carried out in accordance with one of three process embodiments.

The first is, however, limited to methanol. It consists in distilling off the methanol/dimethyl carbonate azeotrope from a mixture, heated to the boiling point, of methanol, alkylene carbonate and catalyst.

According to the second embodiment, alcohol vapor is passed through the alkylene carbonate, which is heated to above the boiling point of the alcohol, and a mixture of the alcohol and dialkyl carbonate is condensed in a collector connected downstream.

Finally, the third method comprises heating the alcohol, alkylene carbonate and catalyst to temperatures above 100°, preferably to 120° to 200° C., and subsequently separating the reaction mixture by distillation.

The reaction can be carried out under normal pressure. A pressure reactor is nevertheless required in the case of low-boiling components if the reaction is to be carried out in the upper temperature range and in the liquid phase. The pressure is not critical. In general, the reaction is allowed to proceed under the autogenous pressure of the reactants. However, the reaction can also be carried out under elevated pressure, for example under an inert gas atmosphere. A pressure of 2 to 100 bars is appropriate here.

The products of the process according to the invention are suitable as solvents for cellulose derivatives and as starting materials for the preparation of diaryl carbonates, aliphatic and aromatic polycarbonates, medicaments and plant protection agents (compare, for example, DT-OS (German Published Specification) No. 2,528,412, DT-AS (German Published Specification) No. 1,031,512, Amer. Chem. Soc. 52, 314 (1930) and Ullmanns Encyklopädie der technischen Chemie (Ullmann's Encyclopaedia of Industrial Chemistry) 3rd edition, volume 9, page 776 et seq.

The process according to the invention can be illustrated in more detail with the aid of the examples which follow, but without being restricted to these examples.

EXAMPLE 1

(a) A mixture of 370 g (4.2 mols) of ethylene glycol carbonate, 672 g (21 mols) of methanol and 0.2 g of thallium carbonate is brought to 150° C. in an autoclave in the course of about 30', whilst stirring and under nitrogen. When this temperature has been reached, a sample is taken and analysed by gas chromatography. It contains 25% by weight of dimethyl carbonate. According to gas chromatography, this content does not change further by extending the reaction time at 150° C. After 2 hours at 150°, the contents of the autoclave are cooled and distilled. In this procedure, methanol and dimethyl carbonate are distilled off from the catalyst very rapidly under normal pressure or under slightly reduced pressure so that the ratio of the reaction components is not shifted by further trans-esterification, and a condensed in cold traps. 731 g of distillate are obtained with a dimethyl carbonate content of 36.0% by weight, that is to say 263 g, corresponding to a conversion of ethylene glycol carbonate to dimethyl carbonate to 70%.

Thereafter, the high-boiling constituent of the reaction mixture, which consists of ethylene glycol and ethylene glycol carbonate, is rapidly distilled off from the catalyst under an oil vacuum up to a sump temperature of 113° and a head temperature of 63°–75°/1.0–1.5 mm Hg. 294 g of distillate are obtained which consists of ethylene glycol to the extent of 62% by weight and ethylene glycol carbonate to the extent of 38% by weight. 0.3 g remains as the distillation residue. This virtually corresponds to the amount of catalyst employed.

The working up loss is about 1.5% by weight, relative to the total reaction mixture. The yield of dimethyl carbonate, relative to ethylene glycol carbonate reacted, is 98–99% of theory.

(b) The mixture (294 g) of ethylene glycol (62%) and ethylene glycol carbonate (38%) obtained from Example 1a is reacted again with 672 g (21 mols) of methanol and the catalyst from 1a which remained as the distillation residue, by bringing the mixture to 150° C. in an autoclave in the course of 30' and cooling it again.

After working up as in 1a, 689 g of a methanol/dimethyl carbonate mixture which contains 89 g of dimethyl carbonate, 267 g of a glycol/glycol carbonate mixture containing 21 g of glycol carbonate, and 0.3 g of distillation residue are obtained, that is to say 80% of the ethylene glycol carbonate taken over from 1a are converted to dimethyl carbonate in this second throughput. The total conversion of glycol carbonate via 1a and 1b is accordingly about 94% and the yield of dimethyl carbonate is 352 g, that is to say 98–99% of theory. Taking into consideration the losses, the yield would be virtually quantitative.

EXAMPLE 2

Example 1a is repeated with the difference that 0.2 g of thallium nitrate is used as the catalyst instead of 0.2 g of thallium carbonate and the reaction is carried out at 180° for 15'. After working up as in Example 1, it is established that the conversion of glycol carbonate is 66% and the distillation residue is 0.25 g. Thus no polyglycols are found. The yield of dimethyl carbonate corresponds to that from Example 1.

EXAMPLE 3 (COMPARISON EXAMPLE)

A mixture as in Example 1a is heated to 150° C. in the presence of 0.15 g of tributylamine (the amount equivalent to 0.2 g of $Tl_2CO_3$) as the catalyst for 2 hours. After working up as under 1a, the following result is found: the reaction mixture is yellowish and the conversion of glycol carbonate is 47%; about 3% thereof have been converted into polyglycols. The distillate contains nitrogen, and thus the catalyst. The rate of trans-esterification is slower than in the case of $Tl_2CO_3$ by a factor of at least 20, the yield of dimethyl carbonate is 3% lower and the separation of the catalyst is more difficult.

EXAMPLE 4 (COMPARISON EXAMPLE)

In order to achieve the same rate of trans-esterification with tributylamine as with $Tl_2CO_3$, the amount of tributylamine must be increased to 5 g, using the same mixture as in Comparison Example 1.

The working up gives the following result: the conversion of glycol carbonate to dimethyl carbonate is 63%. 35 g of polyglycols remain as the distillation residue, that is to say at the same rate of reaction the amine is far less selective than the thallium salt.

EXAMPLE 5

A mixture of 640 g (21.5 mols) of ethanol, 264 g (3.0 mols) of glycol carbonate and 0.1 g of thallium hydroxide is kept at 150° for 2 hours and worked up as in Example 1. A conversion of glycol carbonate to diethyl carbonate of 58% is obtained. The distillation residue is 0.11 g, which corresponds to the amount of catalyst employed; diglycol and triglycol cannot be detected in the distillate.

COMPARISON EXAMPLE

This examples is a repetition of batch 2 in the table in U.S. Pat. No. 3,642,838: a mixture of 640 g (13.9 mols) of ethanol, 264 g (3.0 mols) of glycol carbonate and 3.0 g of sodium ethylate is heated to 200° C. for 3 hours. After cooling, it is worked up as in Example 1. An ethanol fraction (687 g) containing 102 g of diethyl carbonate, corresponding to a conversion of glycol carbonate to diethyl carbonate of 29%, a glycol fraction (113 g, 83° to 102° C./3 mm Hg) and 59 g of residue consisting of viscous polyglycols, from which the glycol fraction can only be distilled out with decomposition occurring, are obtained. The working up and substance loss (splitting off of $CO_2$) is 5% by weight. About 30% of the glycol carbonate employed have been converted into by-products.

EXAMPLE 6

3.52 kg (40 mols) of glycol carbonate, 300 g of methanol and 0.25 g of thallium-I hexahydrobenzoate are heated to 115°-125° C. on a 1.3 m high packed column, whilst at the same time methanol, in each case about 200 g over a period of 20 minutes, is introduced into the reaction mixture via a vaporising flask heated to 210° C. A mixture consisting of dimethyl carbonate and methanol of boiling point 63.7°-64° C. passes over at the head of the column. The dimethyl carbonate content is determined with the aid of a refractive index diagram, plotted from mixtures of known composition. After a reaction time of 22 hours, 10.85 kg of methanol have been introduced and 10.72 kg of distillate with a dimethyl carbonate content of 1.34 kg (14.9 mols) have distilled over. According to analytical determination of the carbonate, the residue (3.2 kg) contains 2.19 kg (24.9 mols) of unreacted glycol carbonate. The glycol carbonate consumption is 15.1 mols. The yield is 99%, relative to glycol carbonate reacted.

EXAMPLE 7

40 mols of glycol carbonate are reacted with 12.4 kg of methanol at an internal temperature of 120°-125° C. in the presence of 1 g of thallium-I nitrate in the course of 32 hours according to Example 6. 1.482 kg=16.5 mols of dimethyl carbonate are contained in the 11.02 kg of azeotropic mixture distilled off. 1.93 kg=22 mols of glycol carbonate remain unreacted. The yield relative to glycol carbonate reacted (18 mols) is thus 92% of theory.

EXAMPLE 8

40 mols of glycol carbonate are reacted with 11.1 kg of methanol at 120°-123° C. in the presence of 0.5 g of thallium-I carbonate in the course of 20 hours according to Example 6. 1.44 kg=16.3 mols of dimethyl carbonate are contained in the 11.16 kg of distillate. 2.02 kg=22.9 mols of glycol carbonate remain unreacted. The yield relative to glycol carbonate reacted (17.1 mols) is thus 96% of theory.

EXAMPLE 9 (COMPARISON EXAMPLE)

40 mols of glycol carbonate are reacted with 12.0 kg of methanol a 120°-123° C. in the presence of 1 g of sodium hydroxide in the course of 32 hours according to Example 7. 1.185 kg=13.2 mols of dimethyl carbonate are contained in the 10.5 kg of azeotropic mixture distilled off. According to $CO_2$ determination by saponification, 1.872 kg=21.3 mols of glycol carbonate remain unreacted in the residue. The yield relative to glycol carbonate reacted (18.7 mols) is 71% of theory.

EXAMPLE 10 (COMPARISON EXAMPLE)

40 mols of glycol carbonate are reacted with 8.5 kg of methanol at 120°-124° C. in the presence of 1 g of lithium hydroxide in the course of 32 hours according to Example 7. 1.162 kg=13.2 mols of dimethyl carbonate are contained in the 7.9 kg of azeotropic mixture distilled off. The residue contains 1.805 kg=20.5 mols of unreacted glycol carbonate. The yield relative to glycol carbonate reacted (19.5 mols) is 68% of theory.

EXAMPLE 11 (COMPARISON EXAMPLE)

40 mols of glycol carbonate are reacted with 9.2 kg of methanol at 120°-125° C. in the presence of 2.5 g of triethanolamine in the course of 32 hours according to Example 7. 1.366 kg=15.1 mols of dimethyl carbonate are contained in the 8.2 kg of distillate. 1.88 kg=20.9 mols of unreacted glycol carbonate are in the residue. The yield relative to the 19.1 mols of glycol carbonate reacted is thus 79% of theory.

EXAMPLE 12

A mixture of 576 g (18 mols) of methanol, 88 g (1 mol) of glycol carbonate and 0.1 g of thallium carbonate is heated to the boil under normal pressure, whilst the dimethyl carbonate/methanol azeotrope is removed at the head of a 1.70 m packed column at 63° C. After 45 hours, the trans-esterification has ended and 290 g of distillate, corresponding to 85.5 g of dimethyl carbonate, have been separated off. In addition to the remaining methanol and the glycol formed, only 0.17 g of diglycol but no polyglycols can be detected in the residue. The yield of dimethyl carbonate is 95% of theory.

If triethylamine is used as the catalyst and it is intended to achieve about the same rate of trans-esterification, 1.5 g, 24 times the equivalent of the above amount of catalyst, are required. The trans-esterification has then ended after 52 hours. The residue contains 1.5 g of diglycol and 0.4 g of triglycol.

EXAMPLE 13

A mixture of 661 g (17.5 mols) of methanol, 457 g (4.48 mols) of propylene carbonate and 0.1 g of thallium carbonate is heated to 150° C. for 2 hours. After cooling and working up as in Example 2, 150 g of dimethyl carbonate are obtained, corresponding to a conversion of propylene carbonate of 32%. The residue is 1 g and the yield of dimethyl carbonate, relative to propylene carbonate reacted, is 98.5%.

What is claimed is:

1. In a process for the preparation of a carbonate by contacting a glycol carbonate of a 1,2-diol with 2 to 4 carbon atoms with an alcohol selected from the group consisting of methanol, ethanol, propanol, isopropanol, n-butanol, isobutanol, allyl alcohol, cyclohexanol, ethylhexanol, benzyl alcohol and methyl-glycol to form the corresponding carbonate of said alcohol at a temperature between 50° and 250° C. in the presence of a catalyst, the improvement wherein a thallium compound is employed as catalyst which thallium compound is selected from the group consisting of thallium-I oxide, thallium-III oxide, thallium-I hydroxide, thallium-I carbonate, thallium-I acetate, thallium-III acetate, thallium-I bromide, thallium-I chloride, thallium-III chloride, thallium-I fluoride, thallium-I formate, thallium-I nitrate, thallium-I cyanate, thallium-I stearate, thallium-I naphthenate, thallium benzoate, thallium cyclohexylphosphonate, thallium-I hexahydrobenzoate, cyclopentadienylthallium, thallium methylate and thallium ethylate.

2. A process according to claim 1 wherein the reaction is carried out at a temperature in the range of from 60° to 220° C.

3. A process according to claim 1 wherein 0.0001 to 10 percent by weight thallium compound, based upon the weight of the reaction mixture, is employed.

4. A process according to claim 1 wherein 0.001 to 1 percent by weight of thallium compound, based upon the weight of the reaction mixture, is employed.

5. A process according to claim 1 wherein between 1 and 10 mols excess alcohol are employed per mol of glycol carbonate.

6. A process according to claim 1 wherein the thallium compound is thallium-I oxide, thallium-I hydroxide, thallium-I carbonate, thallium-I acetate, thallium-III acetate, thallium-I fluoride, thallium-I formate, thallium-I nitrate, thallium-I naphthenate or thallium methylate.

7. A process according to claim 1 wherein the carbonate is butylene glycol carbonate, vinyl ethylene glycol carbonate, chloromethyl ethylene glycol carbonate, ethylene glycol carbonate or propylene glycol carbonate.

* * * * *